(12) United States Patent  
Govari et al.

(10) Patent No.: US 8,000,772 B2  
(45) Date of Patent: Aug. 16, 2011

(54) METAL IMMUNITY IN A REVERSE MAGNETIC SYSTEM

(75) Inventors: Assaf Govari, Haifa (IL); Andres Claudio Altmann, Haifa (IL); Yaron Ephrath, Karkur (IL)

(73) Assignee: Biosense Webster, Inc., Diamond Bar, CA (US)

( * ) Notice: Subject to any disclaimer, the term of this patent is extended or adjusted under 35 U.S.C. 154(b) by 182 days.

(21) Appl. No.: 11/253,913

(22) Filed: Oct. 19, 2005

(65) Prior Publication Data

US 2007/0085528 A1    Apr. 19, 2007

(51) Int. Cl.
*A61B 19/00* (2006.01)

(52) U.S. Cl. .................................................. 600/424

(58) Field of Classification Search ................ 600/409, 600/415, 416, 417, 422, 424; 73/1; 324/200, 324/210, 213, 219, 232, 228, 259, 260
See application file for complete search history.

(56) References Cited

U.S. PATENT DOCUMENTS

| | | |
|---|---|---|
| 4,849,692 A | 7/1989 | Blood |
| 4,945,305 A | 7/1990 | Blood |
| 5,099,845 A | 3/1992 | Besz et al. |
| 5,391,199 A | 2/1995 | Ben-Haim |
| 5,443,489 A | 8/1995 | Ben-Haim |
| 5,558,091 A | 9/1996 | Acker et al. |
| 5,762,064 A | 6/1998 | Polvani |
| 5,767,669 A | 6/1998 | Hansen et al. |
| 6,172,499 B1 | 1/2001 | Ashe |
| 6,177,792 B1 | 1/2001 | Govari et al. |
| 6,201,987 B1 | 3/2001 | Dumoulin |
| 6,373,240 B1 | 4/2002 | Govari |
| 6,453,190 B1 | 9/2002 | Acker et al. |
| 6,690,963 B2 | 2/2004 | Ben-Haim et al. |
| 6,788,967 B2 | 9/2004 | Ben-Haim et al. |
| 6,980,921 B2 * | 12/2005 | Anderson et al. ............. 702/150 |
| 2004/0102696 A1 | 5/2004 | Govari |
| 2004/0207389 A1 | 10/2004 | Nieminen |
| 2004/0239314 A1 | 12/2004 | Govari |
| 2004/0254453 A1 | 12/2004 | Govari |
| 2006/0055712 A1 * | 3/2006 | Anderson ..................... 345/647 |

FOREIGN PATENT DOCUMENTS

EP    0399536 A    11/1990

OTHER PUBLICATIONS

Pending U.S. Appl. No. 10/754,751, Biosense Webster, Inc.
Pending U.S. Appl. No. 11/181,256, Biosense Webster, Inc.
EPO Search Report, 06255366.4-2305, Jan. 30, 2007.
Birkfellner, Wolfgang et al: "Calibration of Tracking Systems in a Surgical Environment"; IEEE Transcations on Medical Imaging; Oct. 1998; vol. 17, No. 5, Piscataway, NJ US.

* cited by examiner

*Primary Examiner* — Tse Chen
*Assistant Examiner* — Elmer Chao
(74) *Attorney, Agent, or Firm* — Louis J. Capezzuto

(57) ABSTRACT

A method for tracking an object includes fixing to the object a transmitter for transmitting a position-indicative magnetic field and providing a map of distortion of the position-indicative magnetic field caused by the object. A distorted magnetic field transmitted from the object is sensed. The distorted magnetic field includes the position-indicative magnetic field subject to the distortion caused by the object. Estimated coordinates of the object based on the sensed, distorted magnetic field are determined. The estimated coordinates and the map are used to compute corrected coordinates.

19 Claims, 5 Drawing Sheets

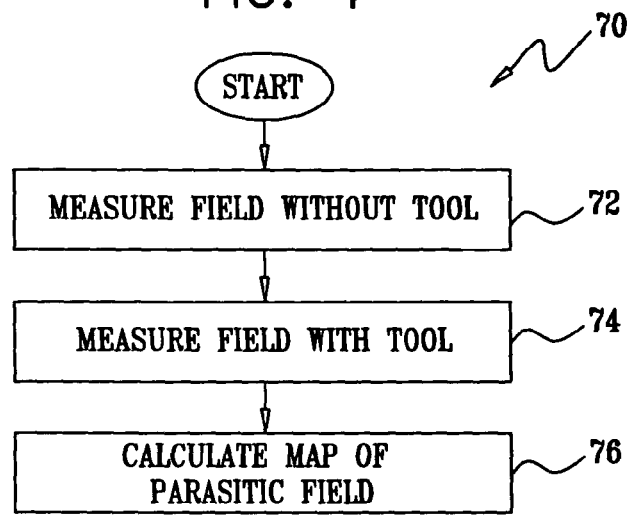
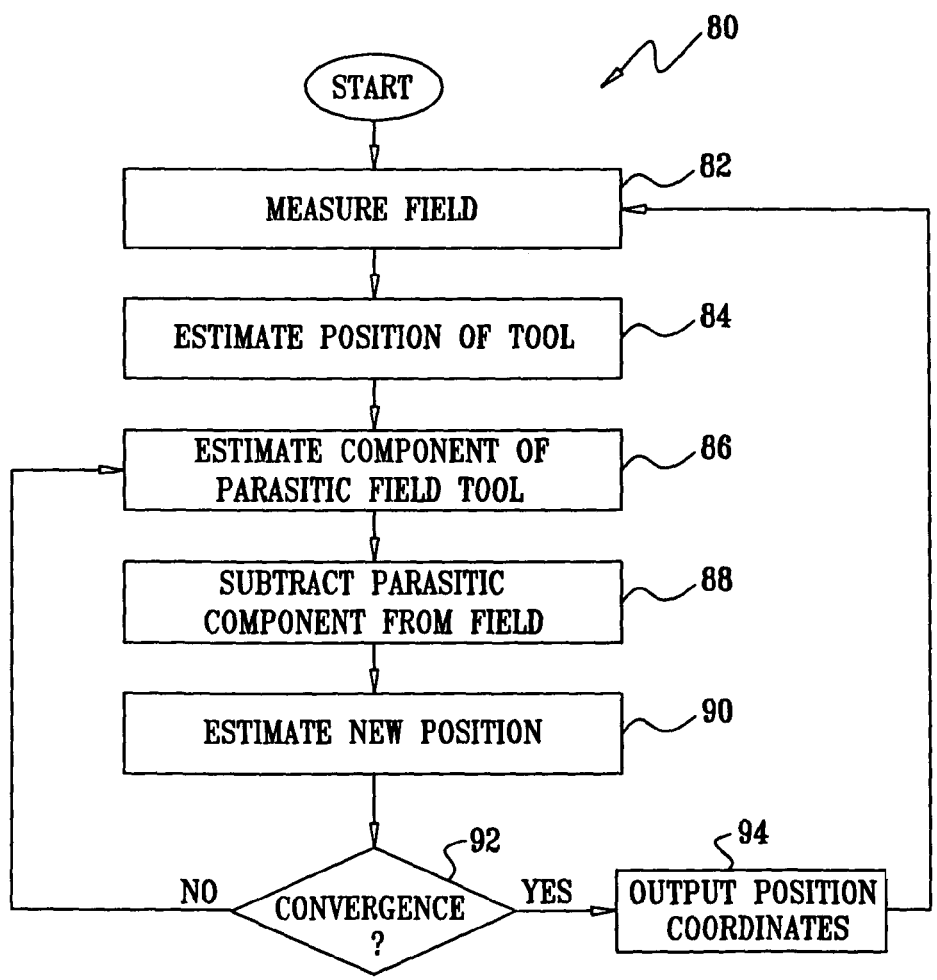

METAL IMMUNITY IN A REVERSE MAGNETIC SYSTEM

FIELD OF THE INVENTION

The present invention relates generally to sensing the position of objects using magnetic fields, and specifically to tracking magnetically-responsive objects during a medical procedure.

BACKGROUND OF THE INVENTION

Magnetic field sensing has become a well-established method for tracking the coordinates of objects involved in medical procedures. Position sensors affixed to the objects being tracked are typically used to measure the relative strengths of externally-generated magnetic fields. These magnetic field measurements are then used to derive object coordinates. Systems operating in this manner are disclosed, for example, in U.S. Pat. Nos. 5,391,199, 5,443,489, and 6,788,967 to Ben-Haim, in U.S. Pat. No. 6,690,963 to Ben-Haim, et al., in U.S. Pat. No. 5,558,091 to Acker et al., and in U.S. Pat. No. 6,177,792 to Govari, all of whose disclosures are incorporated herein by reference.

In alternative systems for magnetic tracking, objects being tracked radiate a magnetic field which is sensed by external receivers. For example, U.S. Pat. No. 5,099,845, to Besz et al., whose disclosure is incorporated herein by reference, describes a location determining device, which has a radiating element forming part of the device to be inserted into an object (such as a human body). The element radiates a signal, which is detected by at least one receiving element. The received signal energy level is used to measure the distance of the radiating element from the receiving element, which is then indicated to an operator in order to locate the device within the object.

U.S. Pat. No. 5,762,064, to Polvani, whose disclosure is incorporated herein by reference, describes a medical magnetic positioning system and method for determining the position of a magnetic probe inside the body. At least two spaced magnetometers are fastened to an area on an external portion of the body proximate to the desired location of the probe inside of the body. The three-dimensional magnetic field of the probe is detected at the magnetometers, and the location of the probe is determined in accordance with the location of the detected three-dimensional field.

U.S. Pat. No. 6,453,190 to Acker et al., whose disclosure is incorporated herein by reference, describes a system in which a field transmitter capable of either detecting or generating a magnetic field is fixed to an instrument at an arbitrary position with respect to a feature of the instrument. A relationship between the instrument feature and the field is calibrated so that the position of the instrument feature may be determined based on the field.

Accurate magnetic field position sensing may be hampered when magnetically-responsive objects, such as metallic tools, enter the space of the magnetic fields. Eddy currents induced in the metallic objects generate parasitic fields that may cause errors in position measurements. Methods for correcting or avoiding these errors have been suggested by prior art. For example, U.S. Pat. Nos. 4,849,692 and 4,945,305 to Blood, whose disclosures are incorporated herein by reference, describe a tracking system that overcomes problems of eddy currents by using pulsed DC magnetic fields. Sensors which are able to detect DC fields are used in the system, and eddy currents are detected by utilizing their decay characteristics and amplitudes.

U.S. Pat. No. 6,201,987, to Dumoulin, whose disclosure is incorporated herein by reference, provides systems for compensating for eddy currents using alternating magnetic field generators. In a first system, compensation for eddy currents is provided by first calibrating the system free from eddy currents, and then modifying the fields generated when the eddy currents are detected. In a second system the eddy currents are nullified by using one or more shielding coils placed near the generators.

U.S. Pat. No. 5,767,669 to Hansen et al., whose disclosure is incorporated herein by reference, describes a method for detecting eddy current distortions in position measurements. The method uses pulsed magnetic fields for position sensing. The rate of change of a sensed field is measured in order to detect eddy currents. Compensation for the eddy current distortions is provided by adjusting the duration of the magnetic pulses.

U.S. Pat. No. 6,373,240 to Govari, whose disclosure is incorporated herein by reference, provides a method for detecting a parasitic field. Parasitic fields generated by a driving signal are shifted in phase relative thereto. A computer process generates driving signals over a range of frequencies. At each frequency, a phase shift is measured in a combined position signal comprising the driving signal and the parasitic field. The computer process determines a frequency that produces a minimum phase-shift, and thus a minimum effect of the parasitic fields. This frequency is used to calculate the position of the object. Alternatively, measurements of the combined signal are made at a plurality of frequencies. The values obtained are used to solve a plurality of simultaneous equations comprising the position signal as one of the unknowns in the equations.

U.S. Pat. No. 6,172,499 to Ashe, whose disclosure is incorporated herein by reference, provides a method for measuring the position and orientation of a receiving antenna. Two or more transmitting antennae of known location and orientation relative to one another are driven by AC excitation. The receiving antennae measure the transmitted AC magnetic fields plus distortions caused by metal objects. Signal processing means are used to ascertain relative values of phase-separated components of the fields to substantially eliminate position errors caused by eddy current distortion.

U.S. Patent Publications 2004/0254453 and 2004/0239314 to Govari, whose disclosures are incorporated herein by reference, provide a position sensing method comprising detection of harmonic frequencies of parasitic fields. A parasitic field generated by a magnetically-responsive element is detected by a pattern of harmonic frequencies indicative of the element. The detected pattern of frequencies is removed from a position signal received by the probe and the resulting clean signal is used to calculate the probe position.

U.S. Patent Publication 2004/0102696 to Govari, whose disclosure is incorporated herein by reference, provides a further method for compensating for parasitic fields. Reference elements placed at known positions near a probe receive position signals indicative of measured reference positions. The measured reference positions differ from the known reference positions due to the interference of parasitic fields. The differences between the measured and the known positions provide a correction factor, which is used to correct a measured position of the probe.

Magnetic-based position sensing systems currently available include products such as the CARTO™ EP Navigation and Ablation System and the LASSO™ Circular Mapping Catheter, produced by Biosense-Webster (Diamond Bar, Calif.).

SUMMARY OF THE INVENTION

In embodiments of the present invention, a magnetically-responsive object, such as a metal tool, is tracked during a medical procedure. Tracking is performed by affixing to the tracked object a miniature magnetic field transmitter. The transmitter radiates a position-indicative magnetic field, which is detected by field sensors in the vicinity of the patient's body.

The magnetic field generated by the transmitter induces eddy currents in the tracked object. The eddy currents, in turn, generate a parasitic magnetic field, which distorts the position-indicative field. Because the transmitter is fixed to the tracked object, however, the physical characteristics (amplitude and direction) of this parasitic field are generally constant relative to the object and may be mapped in advance. The true position of the tracked object is thus determined by subtracting an estimate of the parasitic field, based on a previously-calibrated parasitic field map, from the sensed, distorted field.

Typically, the transmitter fixed to the object is small, and the position-indicative field that it generates is relatively weak and drops strongly with distance from the transmitter. Therefore, this field induces only minimal eddy currents in other magnetically-responsive objects that may be present during the procedure. Consequently, other tools, for example, may be introduced into the vicinity of the medical procedure without affecting the accuracy of the tracking system. One or more additional objects may also be tracked simultaneously without affecting system accuracy.

In some embodiments of the present invention, the map of the parasitic field is measured in a calibration process performed prior to the medical procedure. The calibration process comprises three steps: a first step of measuring an undistorted magnetic field generated by the transmitter when the transmitter is operated without being affixed to a tool; a second step of affixing the transmitter to a tool and measuring a distorted magnetic field that comprises the combination of the undistorted field and a parasitic field due to the tool; and a third step of deriving a map of the parasitic field by subtracting the undistorted field measured in the first step from the distorted field measured in the second step.

After calibration, the parasitic field map may be stored in a control unit that processes the distorted field or in a microcontroller comprised in the transmitter.

Following calibration, an iterative procedure for determining the true position of the tool comprises the steps of: first, estimating an initial position of the tool based on the received magnetic field; second, deriving from the estimated position and from the map of the parasitic field an estimate of the distortion comprised in the received magnetic field; third, removing the estimated distortion from the received magnetic field to derive a less distorted representation of the field; and fourth, deriving a new estimate of the position of the tool from the derived representation of the field. The new position estimate may then be used to improve the estimate of the distortion, and the process may be iterated until the difference between successive position estimates is less than a predetermined threshold.

There is therefore provided, in accordance with an embodiment of the present invention, a method for tracking an object, including:

fixing to the object a transmitter for transmitting a position-indicative magnetic field;

providing a map of distortion of the position-indicative magnetic field caused by the object, referred to a frame of reference of the object;

sensing a distorted magnetic field transmitted from the object, the distorted magnetic field including the position-indicative magnetic field subject to the distortion caused by the object;

determining estimated coordinates of the object based on the sensed, distorted magnetic field; and computing corrected coordinates of the object responsively to the estimated coordinates and to the map.

Typically, computing the corrected coordinates includes replacing the estimated coordinates with the corrected coordinates and performing an iterative calculation to determine an accurate value of the corrected coordinates.

In some embodiments, providing the map of distortion includes applying a calibration procedure to map the distortion associated with the object. Typically, the calibration procedure includes:

placing the object in a jig and measuring the distorted field;

placing the transmitter in the jig, without the object, and measuring an undistorted field; and subtracting the distorted field from the undistorted field so as to derive the map of distortion.

In some embodiments, providing the map of distortion includes providing a table of data points representing the distortion at given spatial coordinates.

Alternatively, providing the map of distortion includes providing a table of parameters of a mathematical model describing the distortion.

Typically, sensing the distorted magnetic field includes measuring an amplitude and a direction of the field so as to determine location and orientation coordinates of the object.

In some embodiments, the method includes generating a graphical output indicative of the position of the object.

Typically, the object is adapted for insertion into a body of a patient, and computing the corrected coordinates includes tracking the object within the body.

There is further provided apparatus for tracking an object, including:

a transmitter, which is adapted to be fixed to the object, and which includes:

transmit antennae operative to transmit a position-indicative magnetic field; and a microcontroller adapted to drive the transmit antennae;

a field sensor, which is adapted to sense a distorted magnetic field including the position-indicative magnetic field subject to distortion caused by the object; and a processor, which is adapted to estimate coordinates of the object based on the sensed, distorted magnetic field and to compute corrected coordinates of the object responsively to the estimated coordinates and to a map of the distortion caused by the object.

Typically, the processor is adapted to replace the estimated coordinates with the corrected coordinates and to perform an iterative calculation to determine an accurate value of the corrected coordinates.

In some embodiments the map of distortion is a table of data points representing the distortion at given spatial coordinates.

Alternatively, the map of distortion is a table of parameters of a mathematical model describing the distortion.

Typically, one of the microcontroller and the processor is adapted to store the map of distortion.

Typically, the field sensor is adapted to sense the distorted magnetic field by measuring an amplitude and a direction of the field so as to determine location and orientation coordinates of the object.

In some embodiments, the processor is adapted to generate a graphical output indicative of the position of the object.

In some embodiments, the object is a metal tool.

The present invention will be more fully understood from the following detailed description of the embodiments thereof, taken together with the drawings in which:

BRIEF DESCRIPTION OF THE DRAWINGS

FIG. 4 is a flow diagram schematically illustrating a method for calibrating a parasitic map, in accordance with an embodiment of the present invention; and FIG. 5 is a flow diagram schematically illustrating a method for tracking a magnetically responsive object, in accordance with an embodiment of the present invention.

DETAILED DESCRIPTION OF EMBODIMENTS

Figure 1:
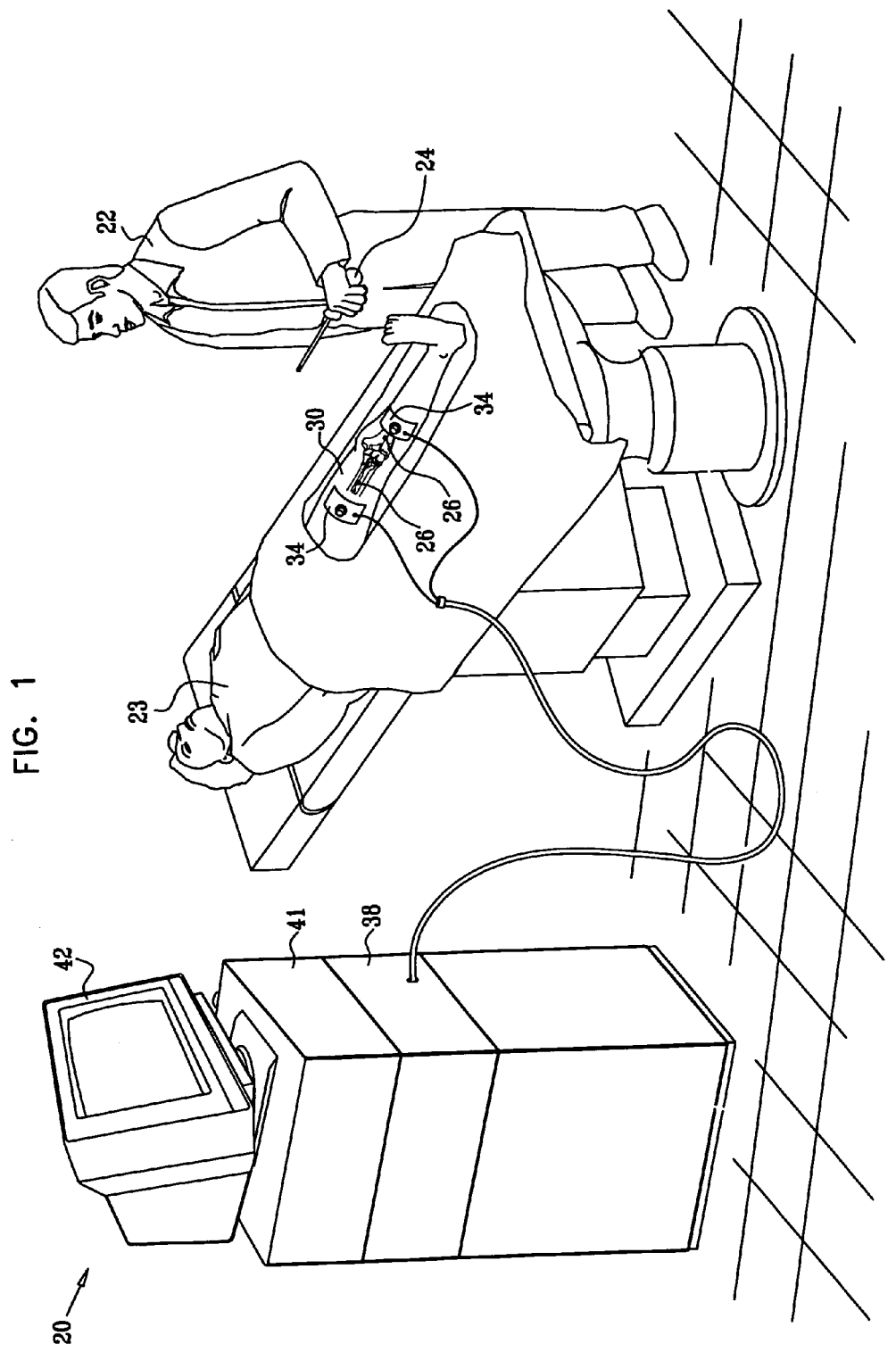
FIG. 1 is a schematic, pictorial illustration of a system for position sensing, in accordance with an embodiment of the present invention.

FIG. 1 is a schematic, pictorial illustration of a magnetic tracking system 20 used in surgery, in accordance with an embodiment of the present invention. A surgeon 22 performs a medical procedure on a patient 23 using a metal tool 24, such as a mallet, chisel, or forceps. Implants 26 may also be introduced into the patient's body at a surgical site, which is located in this example in a leg 30 of the patient. The tracking system guides the surgeon in performing the procedure, in this example a knee-joint operation, by measuring and presenting the positions of tool 24 and implants 26. The system measures the location and orientation coordinates throughout a working volume that comprises the surgical site.

Tool 24 contains a miniature, wireless magnetic field transmitter, which is described in detail hereinbelow. Implants 26 may contain similar transmitters. The position transmitter in tool 24 comprises one or more transmit antennae, described further hereinbelow, which are driven to generate a position-indicative magnetic field. The coordinates of tool 24 are determined relative to field sensors, such as location pads 34, which are fixed to the patient's body and sense the magnetic fields generated by the position transmitters. In the example shown in FIG. 1, the pads are placed on the patient's calf and thigh, in proximity to implants 26. The location pads comprise sensing antennas, such as coils. Alternatively or additionally, the field sensors may be fixed to the operating table or to another structure in the vicinity of patient 23.

The position-indicative magnetic field generated by the position transmitter in tool 24 may induce eddy currents therein. The eddy currents, in turn, generate a parasitic magnetic field that distorts the position indicative field. Location pads 34 detect the distorted field and transmit a corresponding position signal to a control unit, such as signal processing console 38. Console 38 derives the true position of the tool by determining the parasitic field present in the distorted field and subtracting the parasitic field from the distorted field to provide a more accurate representation of the position indicative field. Determination of the parasitic field is facilitated by a parasitic field map obtained in a calibration process described hereinbelow (FIG. 4).

A tracking system computer 41 (which may also perform the functions of console 38) presents the position information graphically to the surgeon on a display 42. For example, the display may show the location and orientation of tool 24 relative to implants 26 as surgeon 22 manipulates the tool during the surgical procedure.

Although the use of system 20 is shown, for the sake of illustration, in the context of orthopedic surgery, the principles of the present invention may similarly be applied in other wireless position sensing systems and applications. For example, transmitters of the type described herein may be incorporated in other types of magnetically-responsive objects used as medical implants and tools, such as catheters for cardiovascular applications, and may likewise be used in non-medical applications.

Figure 2:
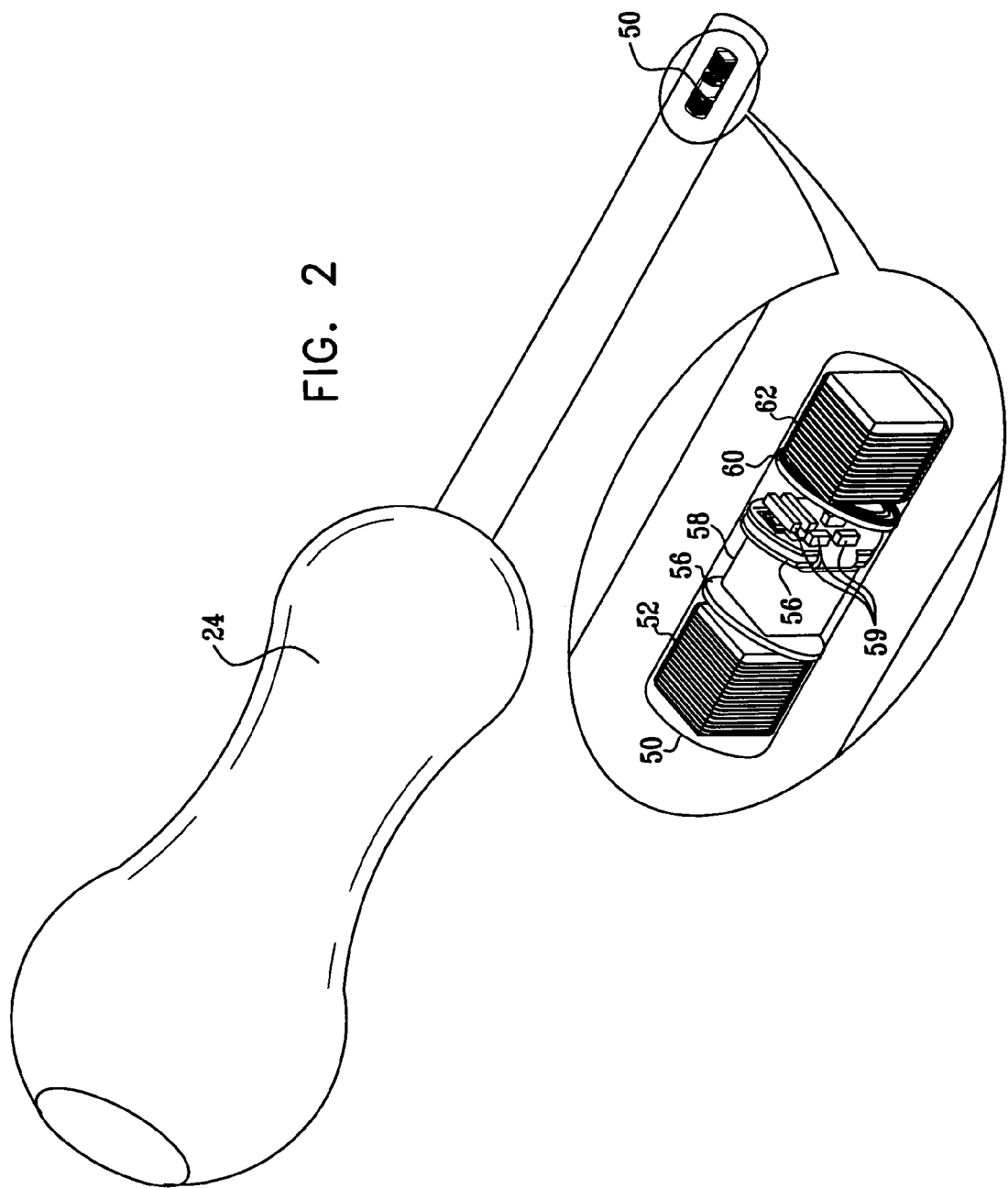
FIG. 2 is a schematic, pictorial illustration showing details of a magnetic field transmitter, in accordance with an embodiment of the present invention.

FIG. 2 is a schematic, pictorial illustration of a position transmitter 50 that is contained in tool 24, in accordance with an embodiment of the present invention. Alternatively, transmitter 50 may be contained in or otherwise attached to other types of tools, implants and other invasive devices. Transmitter 50 in this exemplary embodiment comprises one or more transmit antennae 52, which typically comprise coil wires wound on a magnetic core. Transmitter 50 further comprises one or more power coils 62, and a wireless communication coil 60. The coils are mounted on a suitable substrate 56, such as a flexible printed circuit board (PCB), and are coupled to a microcontroller 58 and peripheral circuit elements 59, which are likewise mounted on the substrate. Transmitter 50 is typically affixed in a cavity in tool 24. Alternatively, the transmitter may be affixed externally to the tool.

Microcontroller 58 drives transmitter coils 52 to generate the position-indicative magnetic fields. The microcontroller is powered by radio frequency (RF) energy received by power coils 62, and is controlled using control signals received by communication coil 60. Typically, the RF energy and control signals are transmitted by location pads 34, in addition to the role of the location pads in sensing the magnetic fields generated by transmitter coils 52. RF energy and control signals may be transmitted, for example, by methods and protocols described in a U.S. patent application Ser. No. 11/181,256, "WIRELESS POSITION TRANSDUCER WITH DIGITAL SIGNALING," filed on Jul. 14, 2005, whose disclosure is incorporated herein by reference.

Further alternatively or additionally, transmitter 50 may comprise a battery (not shown) for powering the microcontroller. As another option, circuit elements 59 may comprise a memory, and the microcontroller may operate independently, based on microcode stored in a memory in the transmitter, without any communication input.

The memory in transmitter 50 may, additionally or alternatively, contain calibration data comprising the parasitic field map, as described further hereinbelow. Alternatively, the calibration data may be stored in a memory of the console 38 and communicated to the transmitter with the control signals.

Although for simplicity, FIG. 2 shows only a single coil in each of the transmitter and power coil assemblies, in practice each assembly typically comprises multiple coils, such as three transmit coils and three power coils. The transmit coils may be wound together, in mutually-orthogonal directions, on one core, while the power coils are wound together, in mutually-orthogonal directions, on another core. Alternatively, the transmit and power coils may be overlapped on the same core, as described, for example in U.S. patent application Ser. No. 10/754,751, filed Jan. 9, 2004, whose disclosure is incorporated herein by reference.

Figure 3A:
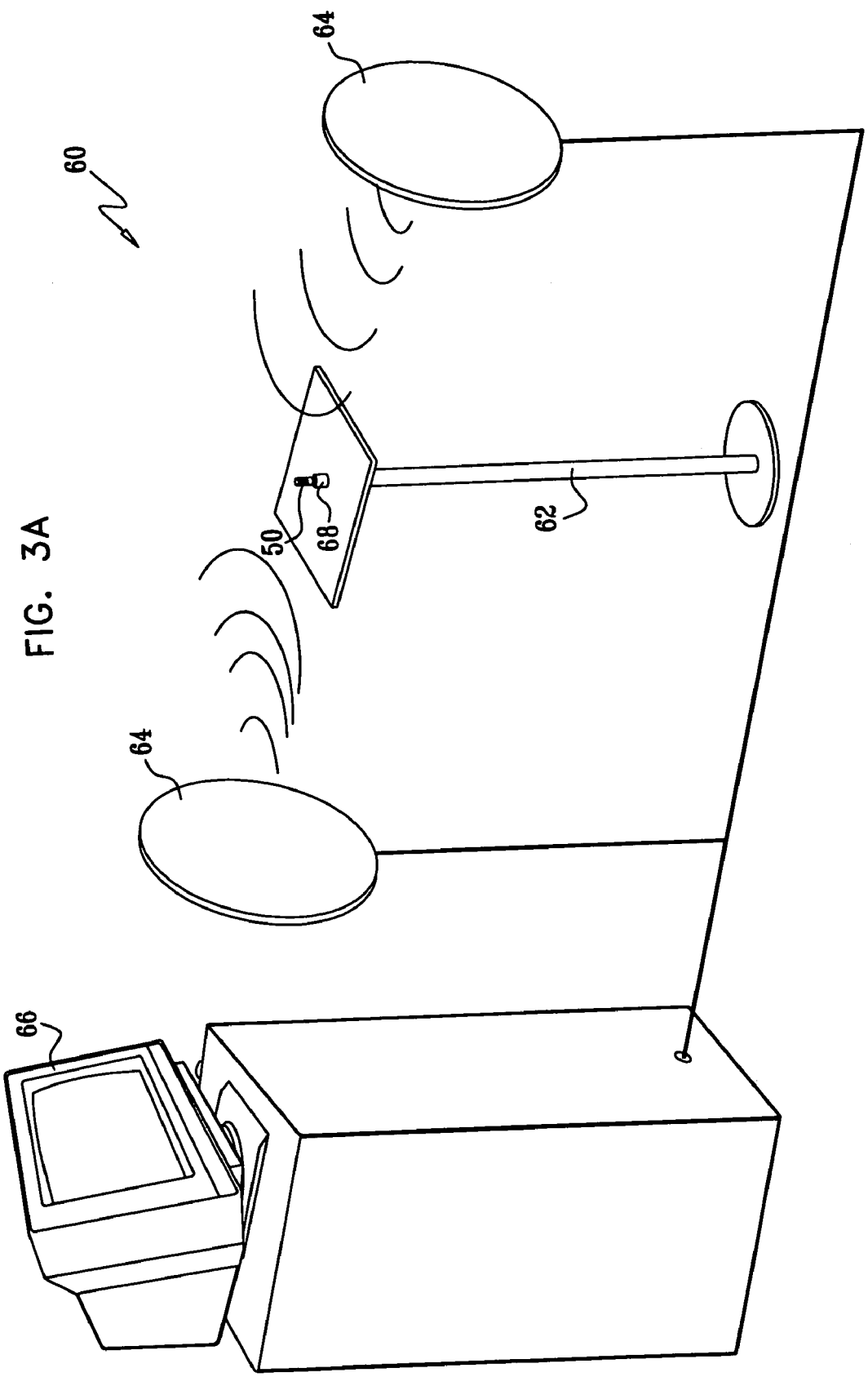
FIGS. 3a and 3b are schematic, pictorial illustrations showing a configuration of calibration apparatus, in accordance with an embodiment of the present invention.
Figure 3B:
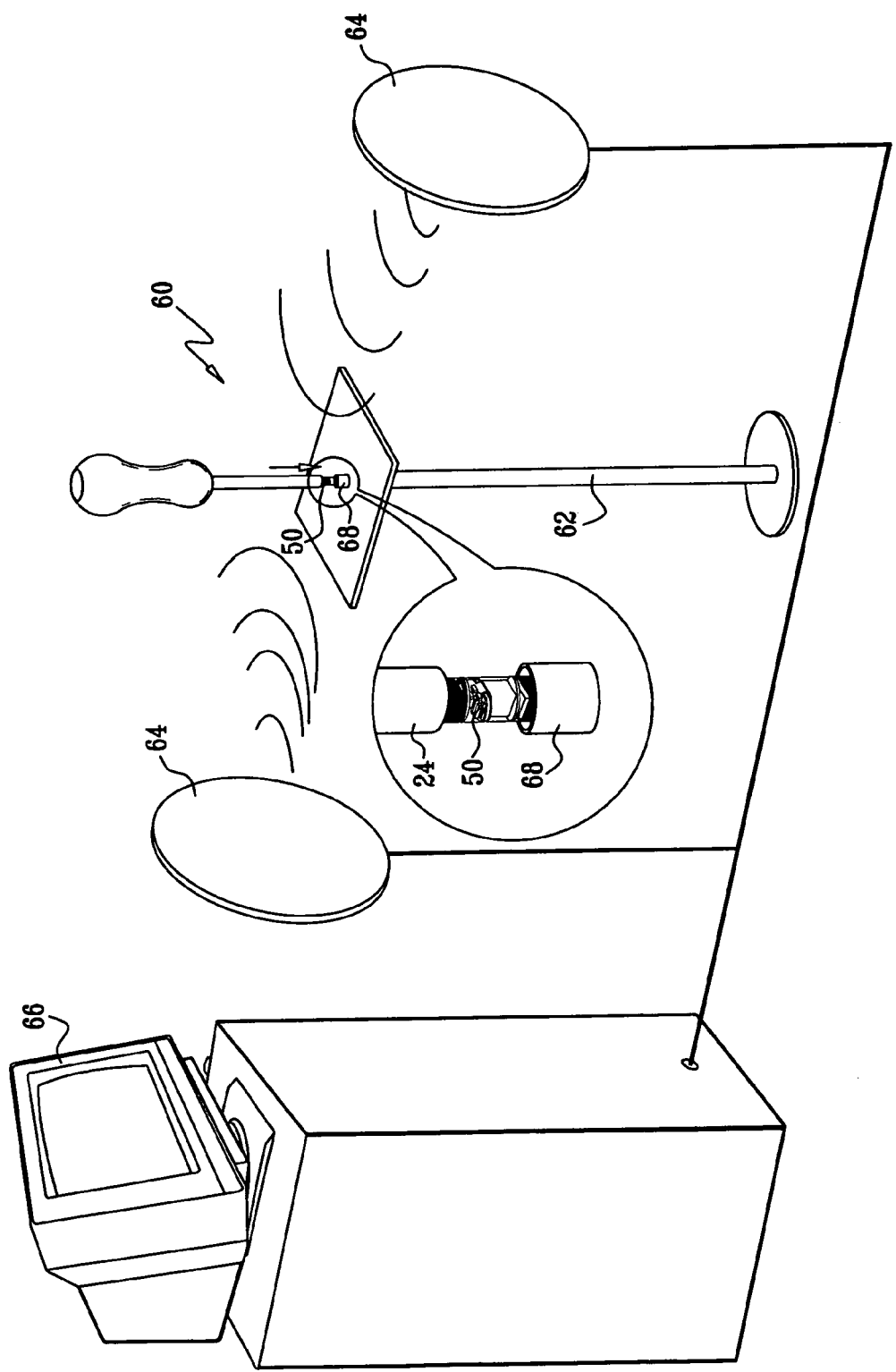

FIGS. 3a and 3b are schematic, pictorial illustrations showing a calibration system 60 used to derive the parasitic field map during the calibration process, in accordance with embodiments of the present invention. Calibration system 60 comprises a non-metallic jig 62, such as the measurement table shown in the figures, and one or more magnetic field calibration sensors 64. Calibration sensors 64 are positioned at known locations and may be moved manually or automatically to additional locations during the calibration process. A calibration computer 66 is coupled to receive signals from calibration sensors 64 that are indicative of the sensed magnetic field. Calibration computer 66 processes the signals to generate calibration data comprising the parasitic field map. Tracking system computer 41 may also perform the functions of calibration computer 66, but tracking system 20 and calibration system 60 are typically distinct, and the calibration data is generally provided in advance of the surgical procedure.

FIG. 3a is an illustration of calibration system 60 being used to calibrate an undistorted magnetic field when transmitter 50 is operated alone without tool 24. Transmitter 50 may be positioned on jig 62 by means of a non-metallic clamp 68, thereby assuring that no metallic objects are in a range to generate a parasitic field. A magnetic field generated by transmitter 50 is detected by calibration sensors 64 and used by computer 66 to generate a map of an undistorted field, according to the calibration process described hereinbelow (FIG. 4).

FIG. 3b is an illustration of calibration system 60 being used to calibrate the distorted magnetic field when transmitter 50 is affixed to metal tool 24. Tool 24 may be positioned on jig 62 by means of non-metallic clamp 68. The magnetic field generated by transmitter 50 creates eddy currents in tool 24, which, in turn, generate parasitic fields that distort the position-indicative magnetic field. The distorted magnetic field is detected by calibration sensors 64 and used by computer 66 to generate a map of the distorted magnetic field. Subsequently, computer 66 derives a map of the parasitic field by subtracting the distorted field from the undistorted field.

FIG. 4 is a flow diagram schematically illustrating a calibration process 70, in accordance with an embodiment of the present invention. Calibration process 70 is typically performed by an equipment manufacturer using calibration system 60, although it can also be performed by an end-user. Calibration data comprising a parasitic field map is determined by calibration process 70 and is subsequently provided for use in a tracking process 80 (FIG. 5). As described hereinabove, the calibration data may be stored in a memory of transmitter 50 or in a memory of the console 38.

At a first step 72 of calibration process 70, transmitter 50 is placed in jig 62 at known spatial coordinates relative to one or more of calibration sensors 64. Transmitter 50 is operated to generate a position-indicative magnetic field, and calibration sensors 64 sense this field without distortion by parasitic fields. Calibration computer 66 acquires signals from the calibration sensors indicative of the undistorted, sensed field and processes the signals to generate a map of the undistorted field relative to the location and orientation coordinates of transmitter 50. The map comprises data points, each of which is a correspondence between a point in space relative to transmitter 50 and a sensed field at that point. Additional data points may be added to the map by moving calibration sensors 64 to additional spatial coordinates relative to transmitter 50, or vice versa, and sensing the undistorted field at the additional spatial coordinates.

At a second step 74, tool 24 containing transmitter 50 is placed in jig 62, and transmitter 50 is operated to generate a position-indicative field. Because the transmitter is affixed to tool 24, eddy currents are induced therein, and a parasitic field is generated. Calibration sensors 64 are operated to sense a distorted field comprising the position indicative field and the parasitic field. Computer 66 acquires signals from calibration sensors 64 indicative of the distorted field, and processes the signals to generate a map of the distorted field relative to the location and orientation coordinates of tool 24. Additional data points may be added to the map by moving calibration sensors 64 to additional spatial coordinates relative to tool 24 and sensing the field at the additional spatial coordinates. Typically, the relative spatial coordinates mapped at step 74 will be the same as those mapped at step 72. Alternatively, different coordinates may be mapped, and a process of interpolation may be used to derive corresponding coordinates.

Subsequently, at a step 76, computer 66 derives a map of the parasitic field by subtracting the field measured at each coordinate in the map of the distorted field from a corresponding measured value in the map of the undistorted field. The map is created in the frame of reference of tool 24, i.e., the map coordinates are referred to the geometry of the tool, rather than some external frame of reference. The map of the parasitic field is made available to system 20 by storing the map in the memory of transmitter 50 or in a memory of the console 38, as described hereinabove. Typically, the map comprises a table of data points relating three-dimensional spatial coordinates in the frame of reference of the tool to three-dimensional values representing the parasitic field at the given spatial coordinates relative to the tool. Alternatively or additionally, calibration computer 66 may compute the map at step 76, in the form of parameters of a mathematical model describing the parasitic field. For example, the data points of the aforementioned map may be used to generate a polynomial equation describing the field. The map is then provided to system 20 in the form of these model parameters.

FIG. 5 is a flow diagram schematically illustrating tracking process 80, in accordance with an embodiment of the present invention.

Typically, tracking process 80 is performed in conjunction with a medical procedure, such as the orthopedic procedure illustrated in FIG. 1. At a field sensing step 82 of tracking process 80, transmitter 50 affixed to tool 24 begins transmission of a position-indicative magnetic field. As noted above, the field is distorted by the parasitic field generated by the tool. Location pads 34 sense the distorted field and send signals indicative of the field to console 38.

At a step 84, console 38 processes the signals and estimates a position of the tool (including both location and orientation coordinates) based on the received field, without compensating for parasitic field effects. Estimation of the tool position is performed by methods of magnetic position sensing, such as those described in the aforementioned U.S. Pat. Nos. 5,391,199, 5,443,489, and 6,788,967 to Ben-Haim.

Next, at a step 86 console 38 uses the estimated position of the tool to estimate a parasitic field component present in the received field. Console 38 uses, as a reference, the parasitic field map for tool 24 that was determined in step 76 of calibration process 70. The console translates and orients the map in space so that the origin and orientation of the map correspond to the location and orientation coordinates estimated at step 84. Interpolation between coordinates of the parasitic field map may be required, as the estimated position of the field sensor relative to the tool may not correspond precisely to a coordinate point provided by the map.

In alternative embodiments of the invention, console 38 may use a map in the form of the above-mentioned mathematical model of the parasitic field to estimate the parasitic field component.

At a subsequent step 88, the estimated component of the parasitic field is subtracted from the distorted field measured in step 82, thereby providing data that is a representation of a less distorted field. This less distorted field data is used as an input to a step 90, which estimates a position of the tool directly from the field data in a manner similar to that used at step 84.

At a decision step 92, the new position estimate derived at step 90 is compared with the prior position estimate to determine whether the estimate has sufficiently converged to be considered accurate. Convergence may be determined by comparing the difference between the new and prior estimates with a preset threshold value, which may be represented by a percent of the estimate or by an absolute spatial distance, such as 0.5 mm. If convergence is sufficient, then the last estimated position derived at step 92 is output at step 94 to tracking computer 41 to be presented graphically to the surgeon on display 42. If convergence at step 92 is determined to be insufficient, then processing continues after step 92 at step 86, and steps 86 through 92 are reiterated until sufficient convergence is achieved. In further embodiments, the tracking computer may also be programmed to determine that further convergence is not possible, and to output a best estimate or an error indication.

After step 94, tracking process continues at step 82, and the tracking process comprising steps 82-94 is repeated as long as tracking is required.

The principles of tracking process 80 may also be applied, mutatis mutandis, to tracking multiple metal objects. A variety of means for differentiating position indicative signals, such as transmission at different frequencies, may be used to identify position-indicative fields and associated parasitic fields of the respective multiple objects.

Because the magnetic field generated by transmitter 50 is weak and short-range, additional, non-tracked metal objects may be introduced into the vicinity of the medical procedure without significantly affecting the accuracy of the tracking system. The eddy currents induced in such additional objects are generally so small that the parasitic fields radiated by the objects are negligible. The invention thus provides a simple means for ensuring metal immunity when multiple metal objects are used in a magnetic-based tracking system.

Moreover, the principles of the embodiments described above may be implemented in conjunction with other position sensing methods known in the art. For example, calibration of the parasitic field may be performed in conjunction with calibration of a feature of the tracked tool, as described in the aforementioned U.S. Pat. No. 6,453,190 to Acker, et al. Both types of calibration may be used by console 38 to determine the position of the tracked tool during the tracking process.

It will thus be appreciated that embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for tracking a metal tool, for use during a medical procedure, comprising:

providing a map of distortion of a position-indicative magnetic field caused by a metal tool in a frame of reference of the tool by applying a calibration procedure to generate a map of the distortion associated with the metal tool, wherein the calibration procedure comprises measuring the distorted field, measuring an undistorted field, and subtracting the distorted field from the undistorted field so as to derive the map of the distortion;

providing a metal tool having a transmitter for transmitting a position-indicative magnetic field;

fixing at least one field sensor within a frame of reference of a medical procedure;

tracking the metal tool as the metal tool moves within the frame of reference of the medical procedure;

sensing a first distorted magnetic field transmitted from the metal tool, the first distorted magnetic field comprising the position-indicative magnetic field subject to the distortion caused by the metal tool within the frame of reference of the medical procedure;

determining estimated coordinates of the metal tool based on the first distorted magnetic field;

estimating the distortion component present in the magnetic field caused by the metal tool being tracked using the map and the estimated coordinates;

determining a second distorted magnetic field by subtracting the estimated distortion component from the first distorted magnetic field; and computing corrected coordinates of the metal tool based on the second distorted magnetic field.

2. The method of claim 1, wherein computing the corrected coordinates comprises replacing the estimated coordinates with the corrected coordinates and performing an iterative calculation to determine an accurate value of the corrected coordinates.

3. The method of claim 1, wherein the calibration procedure comprises:

placing the metal tool in a jig and measuring the distorted field; and placing the transmitter in the jig, without the metal tool, and measuring an undistorted field.

4. The method of claim 1, wherein providing the map of distortion comprises providing a table of data points representing the distortion at given spatial coordinates.

5. The method of claim 1, wherein providing the map of distortion comprises providing a table of parameters of a mathematical model describing the distortion.

6. The method of claim 1, wherein sensing the distorted magnetic field comprises measuring an amplitude and a direction of the field so as to determine location and orientation coordinates of the metal tool.

7. The method of claim 1 further comprising generating a graphical output indicative of the position of the metal tool, based on the corrected coordinates.

8. The method of claim 1, wherein the metal tool is adapted for insertion into a body of a patient.

9. Apparatus for tracking a metal tool for use during a medical procedure, comprising:

a first processor configured to provide a map of distortion of a position-indicative magnetic field caused by a metal tool in a frame of reference of the tool by applying a calibration procedure to generate a map of the distortion associated with the metal tool, wherein the calibration procedure comprises measuring the distorted field, measuring an undistorted field, and subtracting the distorted field from the undistorted field so as to derive the map of the distortion;

a transmitter, adapted to be fixed to a metal tool, the transmitter having a transmit antennae operative to transmit a position-indicative magnetic field and a microcontroller adapted to drive the transmit antennae;

at least one field sensor, adapted to sense a distorted magnetic field comprising the position-indicative magnetic field subject to distortion caused by the metal tool within a frame of reference; and a second processor configured to estimate coordinates of the metal tool as the metal tool moves within the frame of reference, based on a first distorted magnetic field and to compute corrected coordinates of the metal tool responsively to the estimated coordinates and to a map of the distortion caused by the metal tool;

wherein the second processor is adapted to estimate the distortion component present in the magnetic field caused by the metal tool being tracked using the map and the estimated coordinates, and to determine a second distorted magnetic field by subtracting the estimated distortion component from the first distorted magnetic field, wherein the corrected coordinates are computed based on the second distorted magnetic field.

10. The apparatus of claim 9, wherein the processor is adapted to replace the estimated coordinates with the corrected coordinates and to perform an iterative calculation to determine an accurate value of the corrected coordinates.

11. The apparatus of claim 9, wherein the map of distortion is a table of data points representing the distortion at given spatial coordinates.

12. The apparatus of claim 9, wherein the map of distortion is a table of parameters of a mathematical model describing the distortion.

13. The apparatus of claim 9, wherein one of the microcontroller and the processor is adapted to store the map of distortion.

14. The apparatus of claim 9, wherein the field sensor is adapted to sense the distorted magnetic field by measuring an amplitude and a direction of the field so as to determine location and orientation coordinates of the metal tool.

15. The apparatus of claim 9, wherein the processor is adapted to generate a graphical output indicative of the position of the metal tool.

16. The method of claim 1, wherein sensing the distorted magnetic field transmitted from the metal tool comprises sensing a parasitic field in the distorted magnetic field caused by eddy currents induced in the metal tool.

17. The method of claim 16, further comprising fixing an antenna, a power coil, and a communication coil to a flexible printed circuit board, and a processor to the tool.

18. The method of claim 1, wherein sensing the distorted magnetic field transmitted from the metal tool comprises sensing a parasitic field in the distorted magnetic field caused by eddy currents induced in the metal tool and sensing a parasitic field in the distorted magnetic field caused by eddy currents induced in at least a second metal object different than the metal tool.

19. The method of claim 18, wherein the step of sensing the parasitic field in the distorted magnetic field caused by eddy currents induced in at least the second metal object different than the metal tool is sensing the parasitic field in the distorted magnetic field caused by eddy currents induced in at least an implant or a second metal tool.

* * * * *